United States Patent
Otabashi et al.

(10) Patent No.: US 9,796,641 B2
(45) Date of Patent: Oct. 24, 2017

(54) STABILIZATION OF RADIOSYNTHETIC INTERMEDIATES

(71) Applicant: Trasis S.A., Liege (BE)

(72) Inventors: Muhammad Otabashi, Liege (BE); Gauthier Philippart, Hannut (BE); Samuel Voccia, Liege (BE); Ludovic Wouters, Jose (BE); Jean-Luc Morelle, Liege (BE)

(73) Assignee: Trasis S.A., Liege (BE)

( * ) Notice: Subject to any disclaimer, the term of this patent is extended or adjusted under 35 U.S.C. 154(b) by 0 days.

(21) Appl. No.: 14/861,192

(22) Filed: Sep. 22, 2015

(65) Prior Publication Data

US 2016/0075615 A1    Mar. 17, 2016

Related U.S. Application Data

(63) Continuation-in-part of application No. PCT/EP2014/055752, filed on Mar. 21, 2014.

(60) Provisional application No. 61/804,371, filed on Mar. 22, 2013.

(30) Foreign Application Priority Data

Jul. 2, 2013 (EP) .................... 13174707

(51) Int. Cl.
| | |
|---|---|
| *C07C 229/00* | (2006.01) |
| *C07B 63/04* | (2006.01) |
| *A61K 51/04* | (2006.01) |
| *C07C 227/12* | (2006.01) |
| *C07C 227/18* | (2006.01) |

(52) U.S. Cl.
CPC .......... *C07B 63/04* (2013.01); *A61K 51/0402* (2013.01); *C07C 227/12* (2013.01); *C07C 227/18* (2013.01); *C07B 2200/05* (2013.01)

(58) Field of Classification Search
None
See application file for complete search history.

(56) References Cited

U.S. PATENT DOCUMENTS 7,115,766 B2    10/2006   Mulholland et al.

FOREIGN PATENT DOCUMENTS

WO    WO 2005/061415 A1    7/2005

OTHER PUBLICATIONS ("Modify." Merriam-Webster.com. Merriam-Webster, n.d. Web. Jan. 28, 2017.*
Lemaire et al. Journal of Fluorine Chemistry (2012), vol. 138, pp. 48-55.*
Christian Lemaire et al., Highly Enantioselective Synthesis of No-Carrier-Added 6-[$^{18}$F]Fluoro-L-dopa, Eur. J. Org. Chem., 2004, pp. 2899-2904, Wiley-VCH Verlag GmbH & Co. KGaA, Weinheim.
E. Collinson et al., The Action of Ionising Radiations on Organic Compounds, Quarterly Reviews, Jan. 1, 1955, pp. 311-326, Department of Radiotherapeutics, University of Cambridge.
Bertil Waldeck, [$^3$H] Dopa in [$^3$H]tyrosine with high specific activity: a serious complication in the study of catecholamine metabolism, Letters to the Editor, J. Pharm. Pharmac., 1971, pp. 64-65, Department of Pharmacology, University of Goteborg, Goteborg, Sweden.
Franziska M. Wagner et al., Three-Step "One-Pot" Radiosynthesis of 6-Fluoro-3, 4-Dihydroxy-L-Phenylalanine by Isotopic Exchange, The Journal of Nuclear Medicine, Oct. 2009, pp. 1724-1729, vol. 50, No. 10, Society of Nuclear Medicine and Molecular Imaging, Reston, VA.
Bijia Wang et al., Improved Arene Fluorination Methodology for I(III) Salts, Organic Letters, 2010, pp. 3352-3355, vol. 12, No. 15, American Chemical Society.
R. J. Bayly et al., Self-Decomposition of Compounds Labelled With Radioactive Isotopes, Nature, Oct. 29, 1960, pp. 384-387, vol. 188, Nature Publishing Group.
Anthony R. Mazzotti, Palladium (III)-Catalyzed Fluorination of Arylboronic Acid Dervatives, Journal of the American Chemical Society, Sep. 16, 2013, pp. 14012-14015, vol. 135, American Chemical Society.
E.A. Evans, Properties Peculiar to Tritium Compounds, 1974, pp. 642-782, Tritium and Its Compounds, 2nd Edition Butterworths London.
J. K. Thomas et al., Elementary Processes and Reactions in the Radiolysis of Water, Chemistry Division, 49 pages, Argonne National Laboratory, Argonne, Illinois, 1969.

* cited by examiner

*Primary Examiner* — Patrick Lewis
(74) *Attorney, Agent, or Firm* — Reinhart Boerner Van Deuren P.C.

(57) ABSTRACT

The present invention relates to a method for stabilizing radiosynthetic intermediates used in synthesis of $^{18}$F radiolabeled aromatic amino acid derivatives toward decomposition caused by beta and gamma radiations by the use of radical scavengers and/or reductants and/or antioxidants.

7 Claims, No Drawings

STABILIZATION OF RADIOSYNTHETIC INTERMEDIATES

FIELD OF THE INVENTION

The present invention relates to methods for the synthesis of $^{18}$F radiolabeled aromatic amino acid derivatives and more particularly to a method for stabilizing the radiosynthetic intermediates used in said methods toward their decomposition caused by beta and gamma radiations.

BACKGROUND ART

Positron Emission Tomography

Positron emission tomography (PET) is an imaging method for obtaining quantitative molecular and biochemical information of physiological processes in the body. The most common PET radiotracer in use today is [18F]-fluorodeoxyglucose ([18F]-FDG), a radiolabeled glucose molecule. PET imaging with [18F]-FDG allows to visualize glucose metabolism and has a broad range of clinical indications. Other PET radiotracers are about to enter the clinical use. Among positron emitters, $^{18}$F is the most widely used today in the clinical environment.

Decomposition of Radiochemicals—Radiolysis

Radiotracers are obtained after single or multiple step organic synthesis, among which the fluorination with $^{18}$F-fluorides. radiosynthetic intermediates are generally involved in such radiosyntheses. These radiosynthetic intermediates can be exposed to high levels of radioactivity and high dose rates which results in some decomposition processes commonly named radiolysis. These side reactions can consume those radiosynthetic intermediates or react with the $^{18}$F-fluorides and are detrimental to having high radiochemical yields.

The modes by which radiosynthetic intermediates decompose and their corresponding methods of control were classified in 1960 (Bayly, R. J. and Weigel, H., Self-decomposition of compounds labeled with radioactive isotopes. Nature, 188, 384-387 (1960).) (see Table I below).

TABLE I

| Mode of decomposition | Cause | Method of Control |
|---|---|---|
| Primary (Internal) | Natural isotopic decay | None for a given specific activity |
| Primary (External) | Direct interaction of radioactive emission (alpha, beta or gamma) with molecules of the compound | Dilution of the labelled molecules |
| Secondary | Interaction of excited species with molecules of the compound | Dilution of labelled molecules; cooling to low temperatures; free radical scavenging |
| Chemical and microbiological | Thermodynamic instability of compound and poor choice of environment | Cooling to low temperatures; removal of harmful agents |

The compound itself and/or its immediate surroundings will absorb the energy from the radiation. This energy excites the molecules, which can break up or react with other species or compounds. The excited molecular fragments may also react with other labeled compounds producing impurities. Energy absorbed by the immediate surroundings (mainly the solvent) can also produce reactive species, often free radicals, which can subsequently cause destruction of the molecules of radiolabeled compound. Whilst this is occurring, chemical decomposition often takes place as well, as these reactions occur in solution where chemical stability is known to be far more limited.

Secondary Decomposition

This is commonly the greatest path for the decomposition of radiochemicals, and it arises from the interaction of, for example, free radicals created by the radiation energy, with surrounding molecules including the radiolabeled molecules. It is by far the most difficult mode of decomposition to control and it is easily influenced by tiny changes to the environmental conditions. The low chemical content of radiolabeled compounds, particularly at high specific activity, amplifies the problems.

Secondary Decomposition in Water Solutions

The action of ionizing radiation on water is well documented (Thomas, J. K., Elementary processes and reactions in the radiolysis of water. Advances in Radiation Chemistry, 1, 103-198 (1969)). Ionization is known to occur along paths of the beta particles in discrete compartments known as "spurs" (Collison, E. and Swallow, A. J., The action of ionizing radiations on organic compounds. Quarterly Reviews of the Chemical Society, 9, 311-327 (1955)). The most damaging of the reactive species believed to be formed is thought to be the hydroxyl radical (Evans, E. A., Tritium and its Compounds. 2nd edition, Butterworths, London, pp. 642-782 (1974)). This was supported by the hydroxylation reaction of carbon-14 or tritium-labeled phenylalanine, to produce tyrosine and dihydroxyphenylalanine (Waldeck, B., [3H]Dopa in [3H]tyrosine with high specific activity. Journal of Pharmacy and Pharmacology, 23, 64-65 (1971)). In order to lower the decomposition, it is necessary to avoid or lessen the interactions between the damaging radicals and the surrounding molecules including the radiolabeled molecules. This can be achieved by lowering the temperature, diluting the radioactive concentration, and by adding radical scavengers. Ethanol is a common radical scavenger (typically as a 2% solution in water).

Secondary Decomposition in Organic Solvents

The detailed mechanism of decomposition of radiochemicals in organic solvents is not well known, and is expected to be complex. The effect of radiation energy on organic solvents is expected to be very different than that of aqueous media and would produce different forms of reactive species. The chemical purity of the solvent is for sure a critical parameter and well purified or very high quality purchased solvents ought to be used. The presence of peroxide in the solution may cause total destruction of the surrounding molecules including the radiolabeled molecules.

[18F]-Radiolabeled Aromatic Amino Acid

Radiolabeled aromatic amino acid derivatives, such as 18F-FDOPA, 18F-FTYR, 18F-FmTYR, etc. are often used to monitor the metabolism in the dopaminergic system. These radiotracers can be indicated to monitor Parkinson disease (PD), Alzheimer disease (AD) and some neurodegenerative diseases. These radiotracers have also shown interest in medical imaging of neuroendocrine tumors (NET).

Radiolabeled aromatic amino acid derivatives can be synthesized following different methods or paths such as for example:

Lemaire et al.
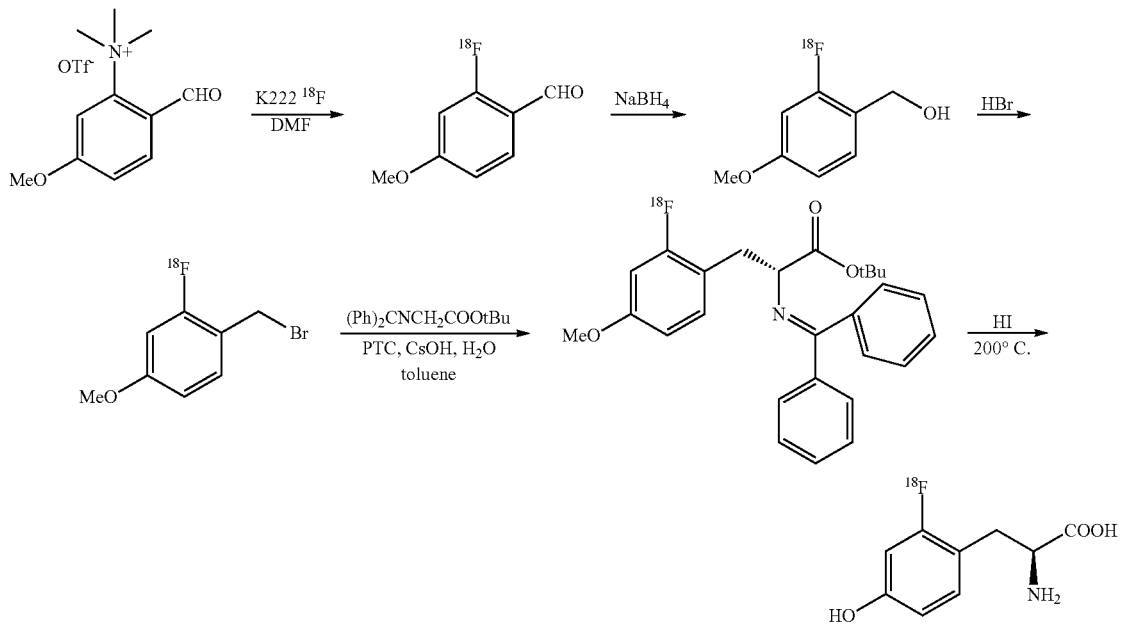
Di Magno et al.
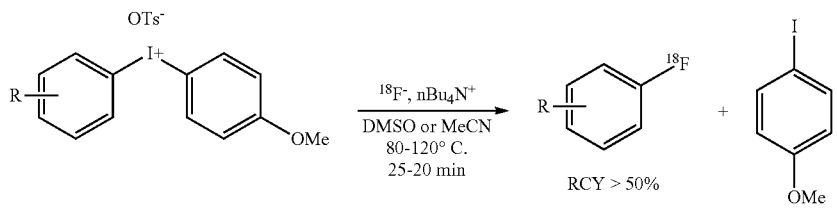
R = OMe, Me, H, Br or Cl
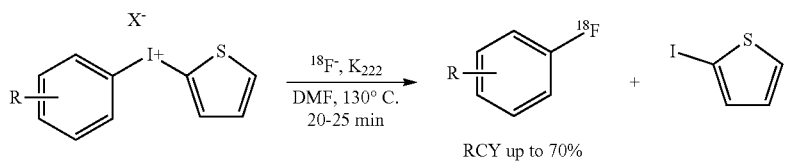
R = H, 4-Me, 2-OMe, 3-OMe, 4-OBn, 4-I, 4-Br, 4-Cl
X = Br, OTs, OTf
Coenen et al.
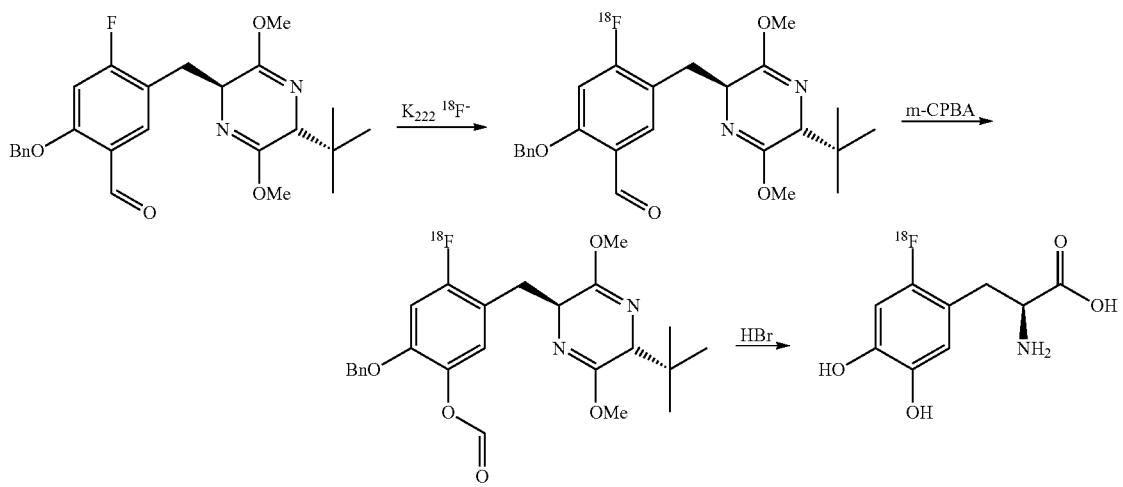

Mulholland et al.
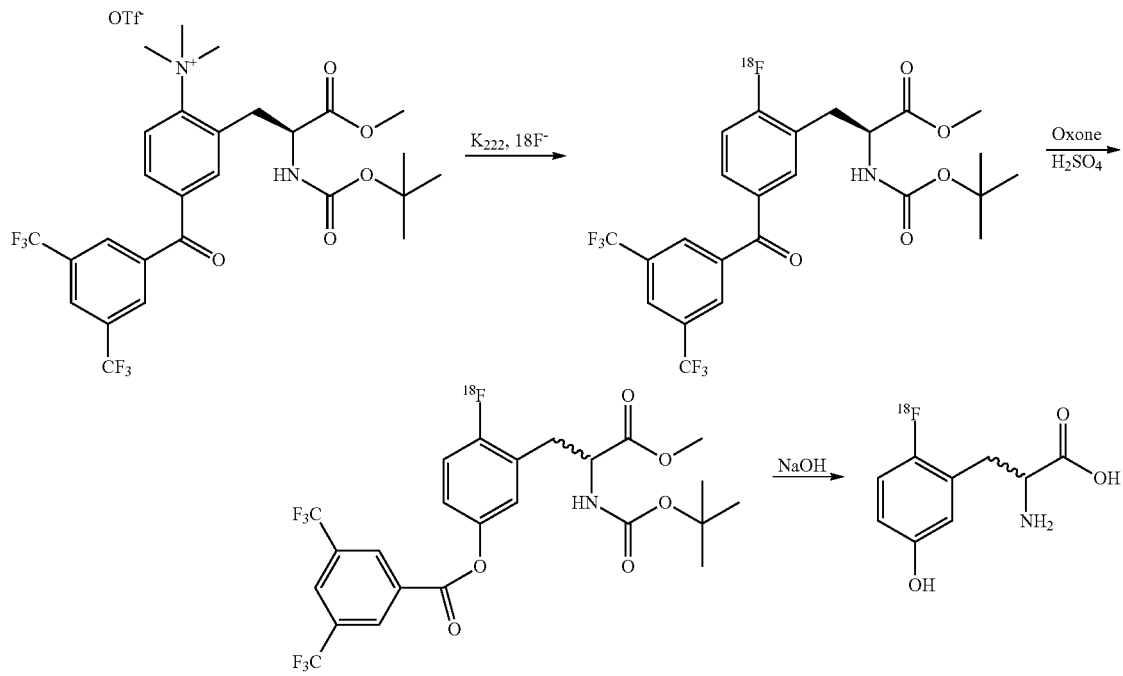
Ritter et al.
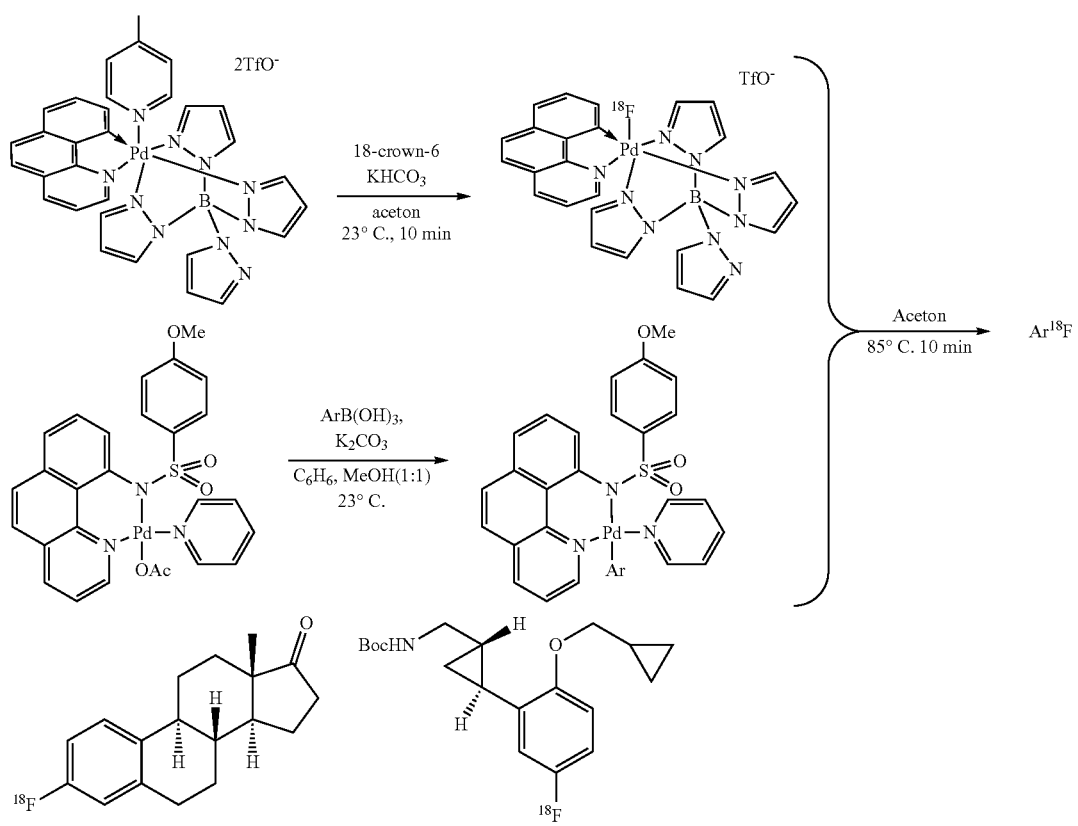

Electrophilic synthesis from $^{18}F_2$

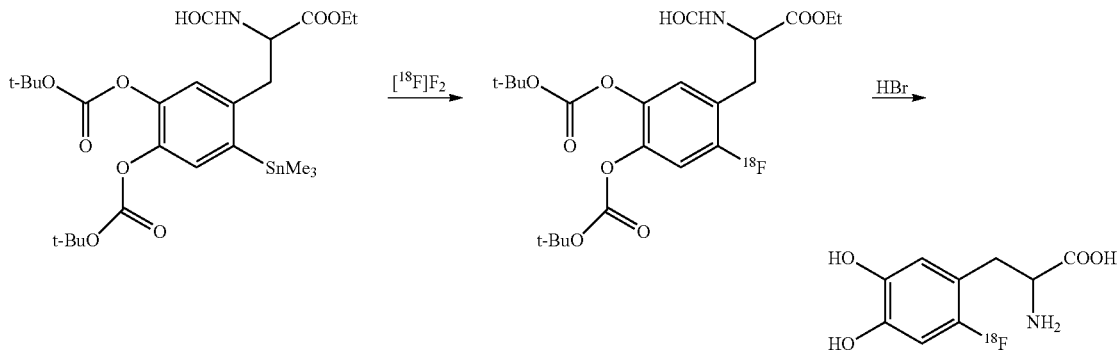

However, most of these syntheses show drops in the radiochemical yields at high level of radioactivity due to the instability of the benzylic and/or phenolic radiosynthetic intermediates.

PROBLEM TO BE SOLVED

Benzylic and Phenolic Radiosynthetic Intermediates

The instability toward radioactivity and especially beta and gamma radiations may be attributed to the presence of the aromatic ring (see above reactivity toward hydroxyl radicals), but also to the benzylic or phenolic positions that are present whatever the synthesis path (as shown above) chosen for radiolabeled aromatic amino acid synthesis.

These reactive sites can be subjected to side reactions that will consume the radiosynthetic intermediates, including cold intermediates such as the precursor to be radiolabelled, that become unavailable for the subsequent chemistry steps. This is detrimental for having high radiosynthesis yields in the radiopharmacies where starting activity is in the range of 1-30 Ci, i.e. radioactivity concentrations from 0.5 to 15 Ci/ml.

Document WO 2005/061415 A1 discloses the preparation of a resin-bound benzylic intermediate (example 13). This compound is used as an intermediate in the synthesis of 18F-labeled FDOPA (example 11). 2,2,6,6-tetramethylpiperidin-1-yl)oxidanyl (TEMPO) is used as a stabilizing agent. In this context ascorbate is also known to be a free radical trap.

AIM OF THE INVENTION

The present invention aims at avoiding decomposition reactions, i.e. radiolysis resulting from high radioactivity concentrations, of radiosynthetic intermediates used in the synthesis of $^{18}F$ labeled aromatic amino acids by the use of radical scavengers or reductants or antioxidants during the crucial steps of the radiochemical synthesis. In other words, the invention aims at stabilizing the radiochemical yields of radiochemical synthesis of aromatic amino acids whatever the level of starting radioactivity used.

DISCLOSURE OF THE INVENTION

The present invention relates to the stabilization toward radiolysis of radiosynthetic intermediates, including cold intermediates such as the precursor to be radiolabelled, by the use of radical scavengers or reductants or antioxidants during the steps where high radioactivity concentrations are involved. The decomposition is especially important when water is present, where the presence of highly reactive hydroxyl radicals decomposes the radiosynthetic intermediates.

The present invention focuses on radiosynthetic intermediates involved in the synthesis of $^{18}F$ radiolabeled aromatic amino acids derivatives, including cold molecules such as the prescursor to be radiolabelled, because of the instability of the aromatic ring and of the benzylic and phenolic species involved in these syntheses.

The general structure of the radiosynthetic intermediates that needs to be stabilized in the context of the present invention can be as follows:

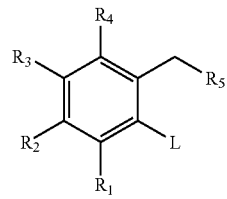

with $R_1$, $R_2$, $R_3$, $R_4$, $R_5$ and L as follows:

$R_1$, $R_2$, $R_3$, $R_4$=H, OMe, OBn, Oallyl, H, OH;
L=$NO_2$, $NMe_3^+$, F, $^{18}F$, $IO_2$

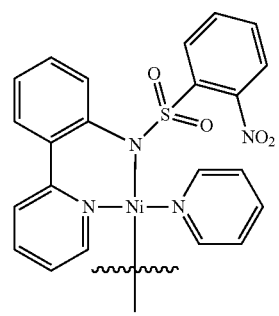

-continued

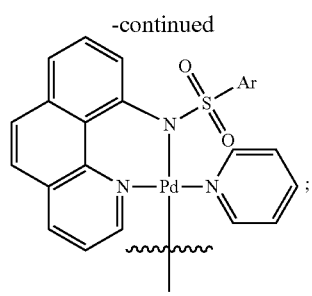

and
R$_5$=OH, I, Br, Cl

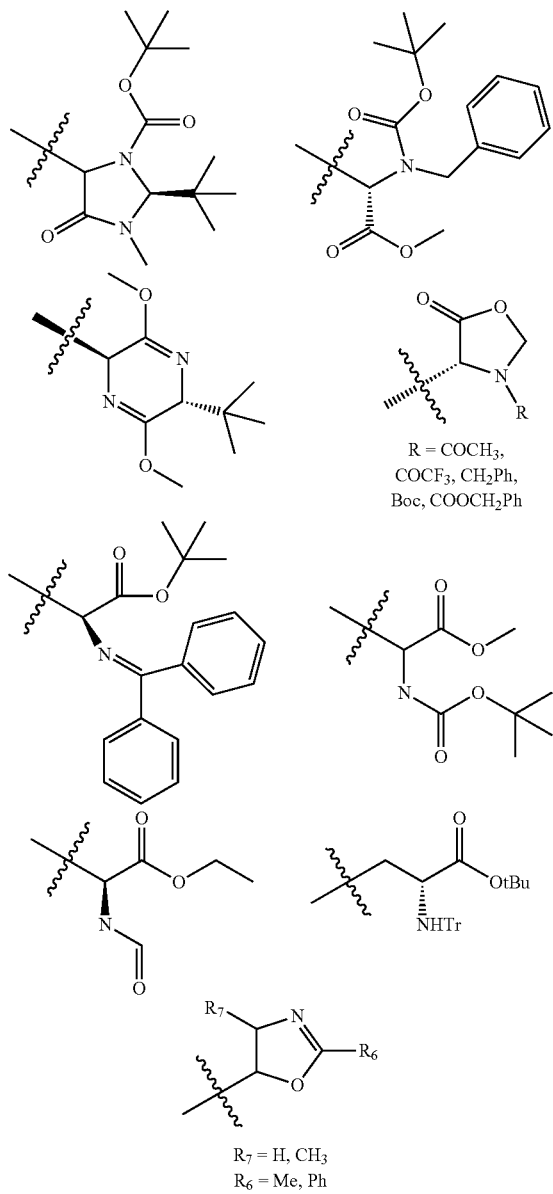

R = COCH$_3$,
COCF$_3$, CH$_2$Ph,
Boc, COOCH$_2$Ph

R$_7$ = H, CH$_3$
R$_6$ = Me, Ph

Due to the side reactions that are involved during the decomposition of the radiosynthetic intermediates, the "stabilizer" used during the radiosynthetic process according to the present invention can either be:

a radical scavenging species;
a reductant species;
an antioxidant species;
a species with more than one of the characteristics above.

In some preferred embodiments of the present invention, carbonate ($CO_3^{2-}$), nitrite, thiosulfate, thiosulfite, phosphate, phosphite or hypophosphite is used for the stabilization of the radiosynthetic intermediate.

In some preferred embodiments of the present invention, phosphorous acid is used for the stabilization of the radiosynthetic intermediate.

In some preferred embodiments of the present invention, a Fe(II) derivative or a Sn(II) derivative is used for the stabilization of the radiosynthetic intermediate.

In some preferred embodiments of the present invention, a phenol derivative is used for the stabilization of the radiosynthetic intermediate.

In some preferred embodiments of the present invention, iodide is used for the stabilization of the radiosynthetic intermediate.

In some preferred embodiments of the present invention, the compound used for the stabilization is also involved in the radiosynthetic process as a reagent or as a solvent.

In some preferred embodiments of the present invention, HI is used as for the stabilization of the radiosynthetic intermediate but also as a reagent and can be involved in chemical reactions such as halogenation or hydrolysis/deprotection.

In some preferred embodiments of the present invention, toluene is used for as a solvent for the stabilization of the radiosynthetic intermediate.

In some preferred embodiments of the present invention, dichloromethane is used for as a solvent for stabilization of the radiosynthetic intermediate.

EXAMPLES

In these examples it will be demonstrated how the right choice of the additives and reagents allows to stabilize the yields toward increasing the starting activity.

Example 1

[18F]-FDOPA Synthesis with Lemaire et al. Method and with Eliminating HI in the Crucial Step

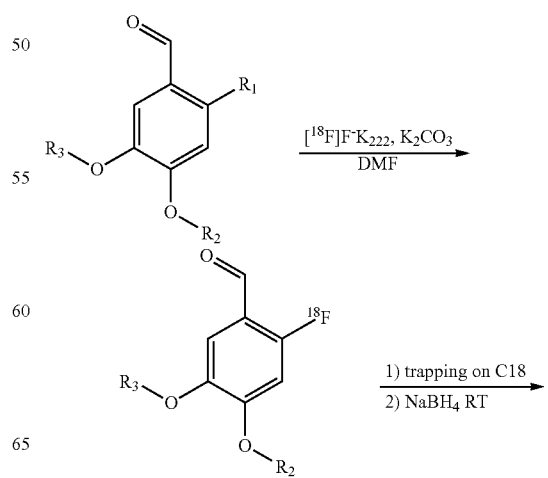

-continued

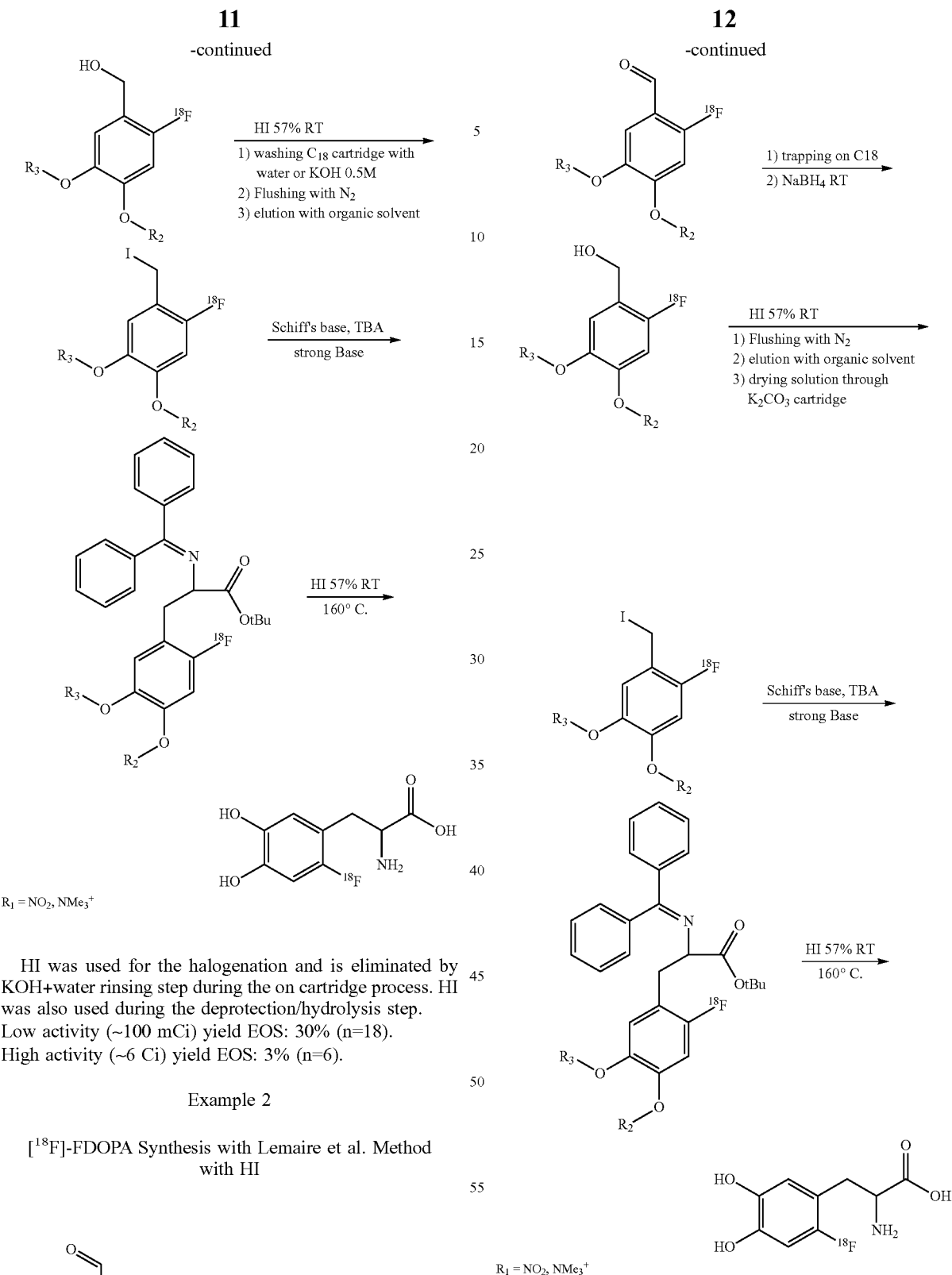

$R_1 = NO_2, NMe_3^+$

HI was used for the halogenation and is eliminated by KOH+water rinsing step during the on cartridge process. HI was also used during the deprotection/hydrolysis step.
Low activity (~100 mCi) yield EOS: 30% (n=18).
High activity (~6 Ci) yield EOS: 3% (n=6).

Example 2

[$^{18}$F]-FDOPA Synthesis with Lemaire et al. Method with HI

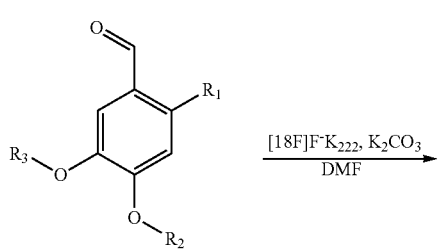

HI was used for the halogenation and remains present all the time during the on cartridge process. HI was also used during the deprotection/hydrolysis step.
Low activity (~100 mCi) yield EOS: 25% (n=20).
High activity (~6 Ci) yield EOS: 25% (n=10).

Example 3

[18F]-FDOPA Synthesis with Lemaire et al. Method with Replacement of HI with HBr in the Crucial Step

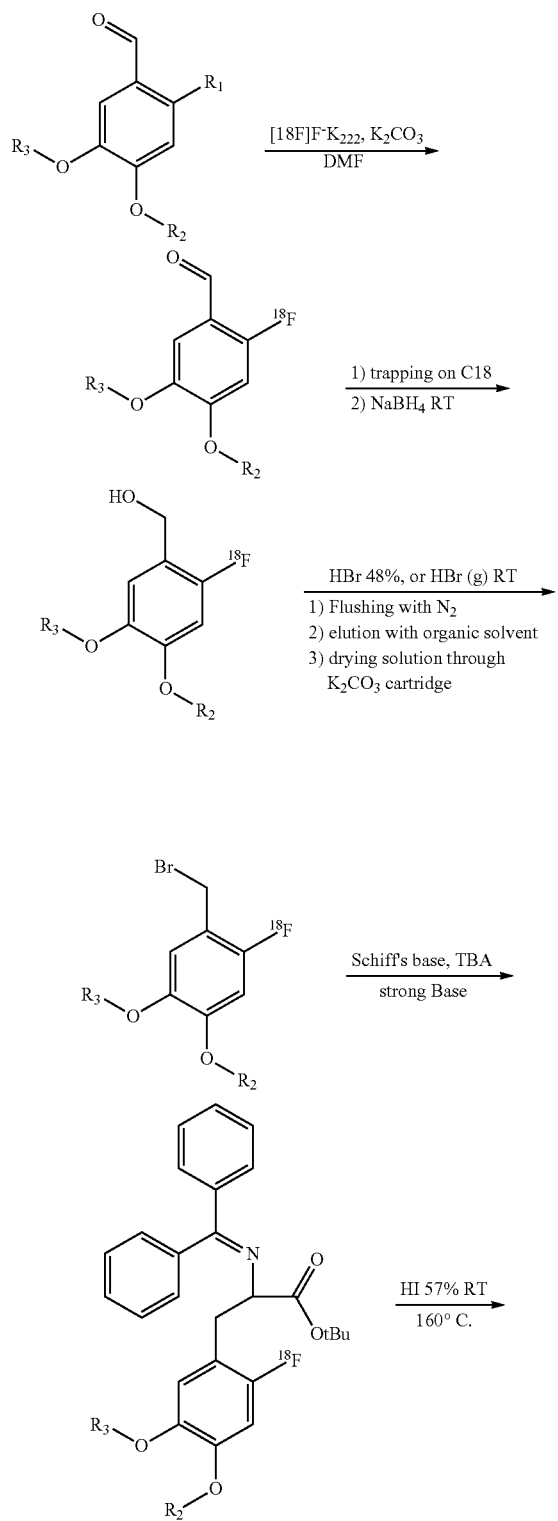

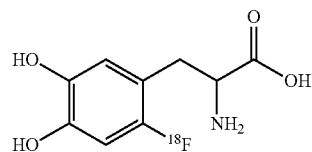

$R_1 = NO_2, NMe_3^+$

HBr was used for the halogenation HI was used during the deprotection/hydrolysis step.

Low activity (~100 mCi) yield EOS: 20% (n=3).
High activity (~3 Ci) yield EOS: 12% (n=2).

Example 4

[18F]-FDOPA Synthesis with Lemaire et al. Method with Replacement of HI with HBr/KI in the Crucial Step

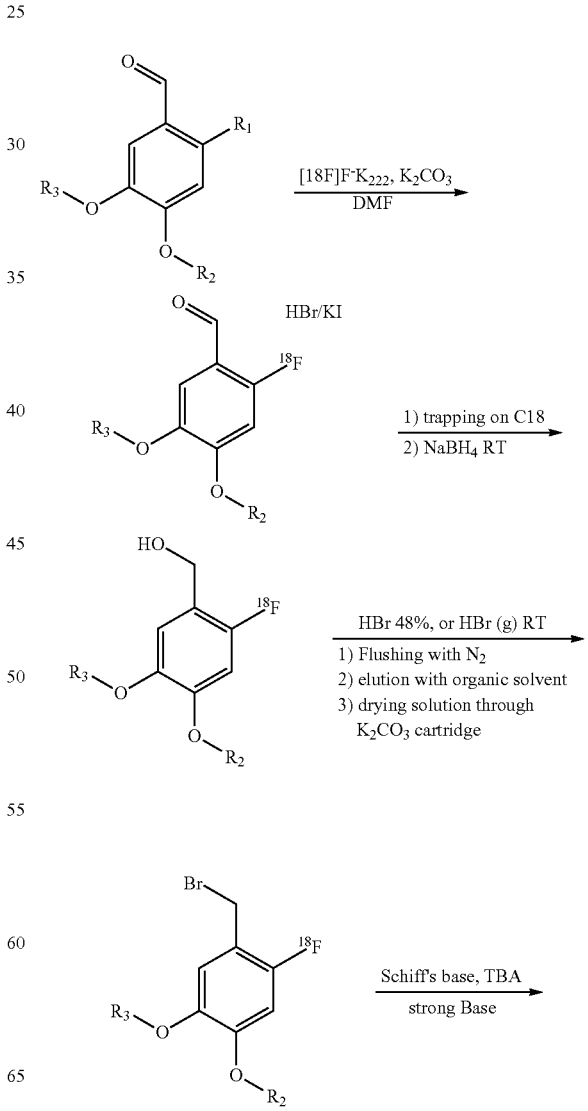

-continued

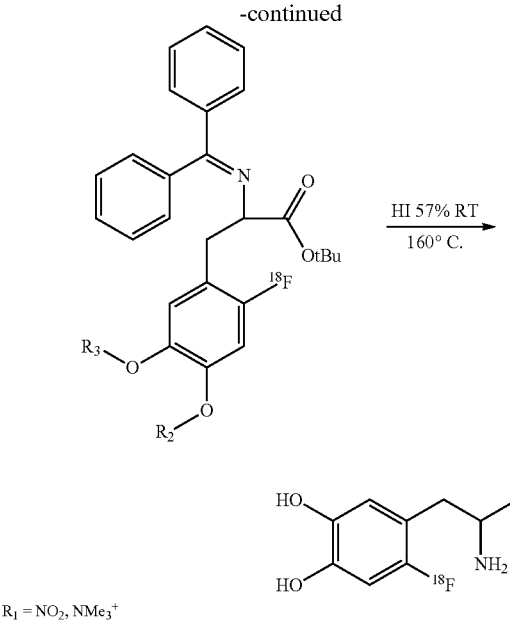

$R_1 = NO_2, NMe_3^+$

HBr was used for the halogenation in mixture with KI. HI was used during the deprotection/hydrolysis step.
Low activity (~100 mCi) yield EOS: 21% (n=3).
High activity (~3 Ci) yield EOS: 19% (n=2).

Example 5

[18F]-FDOPA synthesis with Di Magno et al. method and HBr

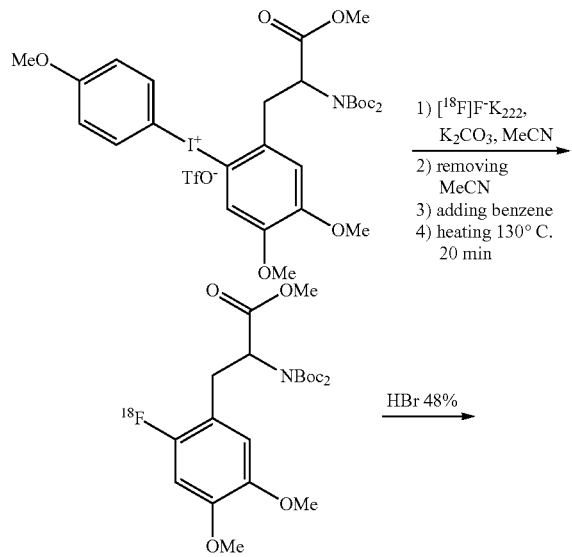

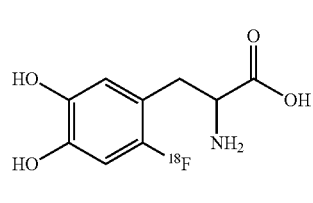

HBr was used during the deprotection/hydrolysis step.
Low activity (~100 mCi) yield EOS: 18% (n=2).
High activity (~1.5 Ci) yield EOS: 9% (n=1).

Example 6

[18F]-FDOPA Synthesis with Coenen et al. Method and HBr

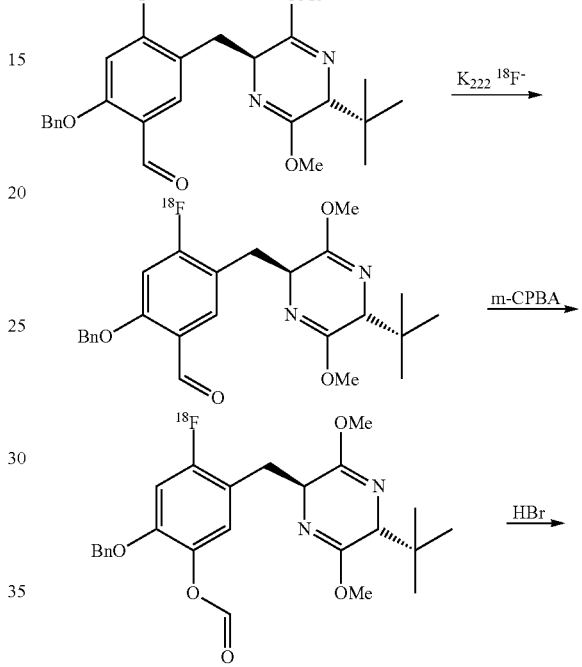

HBr was used during the deprotection/hydrolysis step.
Low activity (~60 mCi) yield EOS: 15% (n=1).
High activity (~3 Ci) yield EOS: 8% (n=1).

Example 7

[18F]FDOPA Synthesis with Coenen et al. Method and HBr/KI

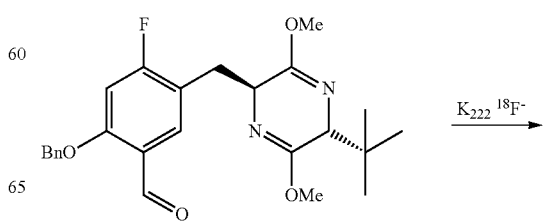

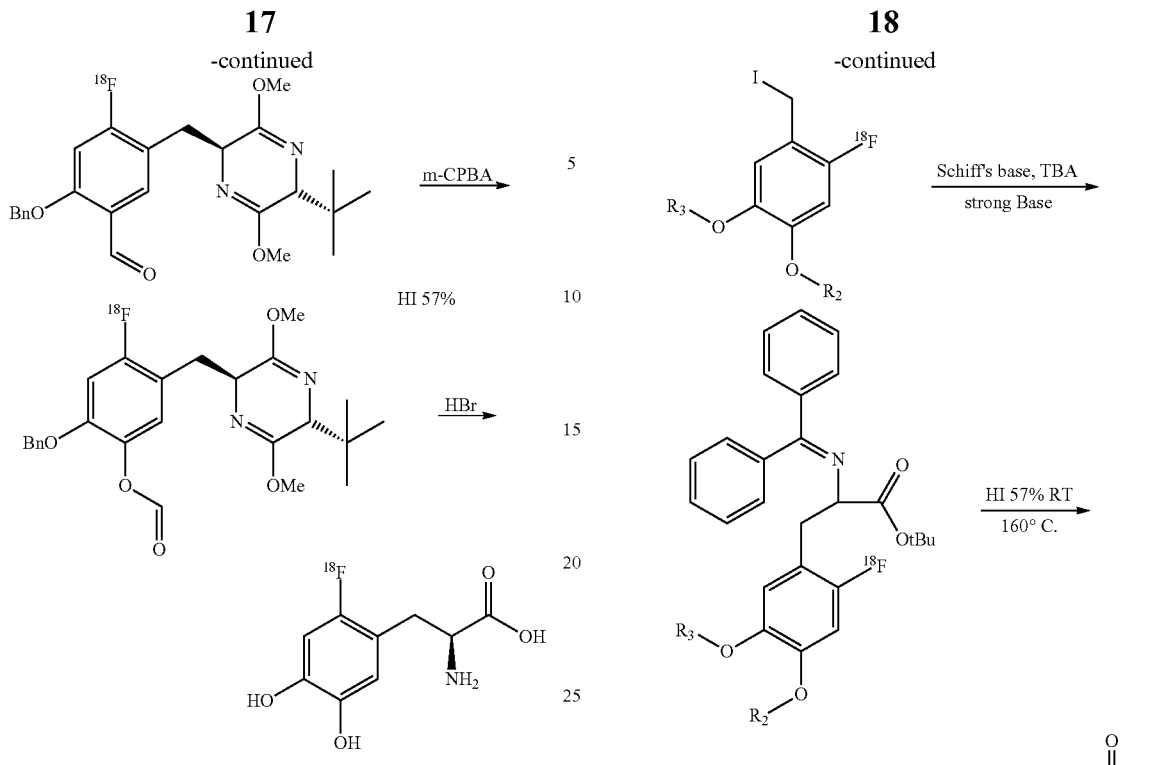

HBr/KI was used during the deprotection/hydrolysis step.
Low activity (~50 mCi) yield: 12% (n=1).
High activity (~3 Ci) yield: 11% (n=1).

Example 8

[18F]-FDOPA Synthesis with Lemaire et al. Method and with Eliminating HI in the Crucial Step in the Presence of Sodium Thiosulfate (STS)

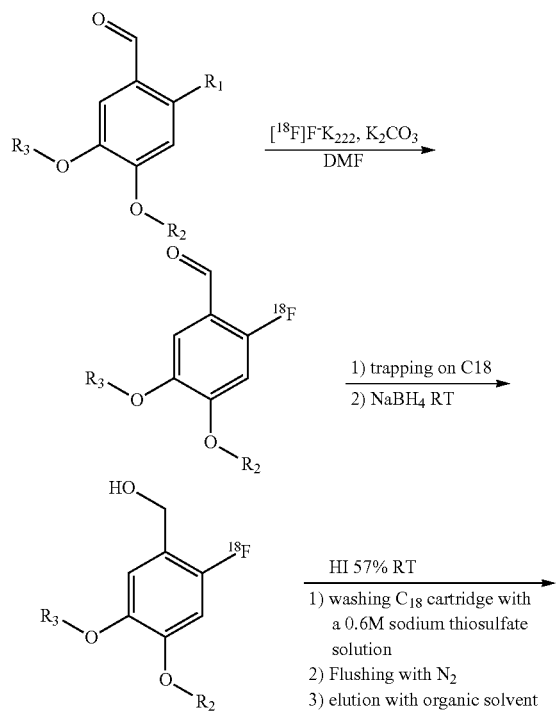

HI was used for the halogenation and is eliminated by a sodium thiosulfate in water solution rinsing step during the on cartridge process. HI was also used during the deprotection/hydrolysis step.
Low activity (~45 mCi) yield EOS: 23% (n=1).
High activity (~3 Ci) yield EOS: 19% (n=1).

The invention claimed is:
1. A method for stabilizing, toward decomposition caused by beta and gamma radiations, cold and radiosynthetic intermediates used in a synthesis of 18F radiolabeled aromatic amino acid derivatives, wherein the starting activity of 18F is in the range 1-30 Ci for a radioactivity concentration from 0.5 to 15 Ci/mL, said synthesis comprising at least the steps of:
  1) providing a cold aromatic precursor;
  2) fluorinating said cold aromatic precursor with 18F so as to obtain a 18F radiosynthetic intermediate, and modifying said 18F radiosynthetic intermediate, or
  2) modifying said cold aromatic precursor so as to obtain a cold aromatic intermediate, and fluorinating said cold aromatic intermediate with 18F, so as to obtain in both cases a modified 18F radiosynthetic intermediate, wherein the step of modifying said cold aromatic precursor or 18F radiosynthetic intermediate is at least one of a reduction, an oxidation, a halogenation reaction, and a substitution reaction of one functional group by another functional group;
  3) deprotecting and/or hydrolyzing said modified 18F radiosynthetic intermediate so as to obtain said 18F radiolabeled aromatic amino acid derivative, said cold aromatic precursor, said cold aromatic intermediate, and said modified or not 18F radiosynthetic intermediate having the general structure:

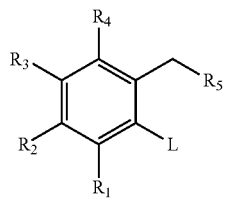

wherein $R_1$, $R_2$, $R_3$, and $R_4$ are selected from the group consisting of H, OH, OMe, OBn, and Oallyl;

wherein L is selected from the group consisting of $NO_2$, $NMe_3^+$, F, $IO_2$,

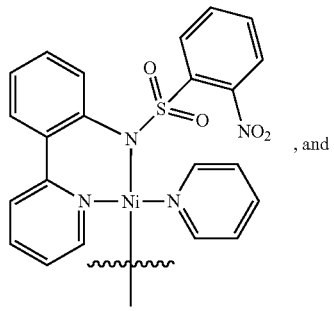, and

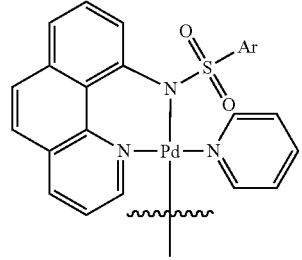

in the case of a cold aromatic precursor or a cold aromatic intermediate and wherein L is $^{18}F$ in the case of a modified or not 18F radiosynthetic intermediate;

wherein $R_5$ is selected from the group consisting of OH, I, Br, Cl,

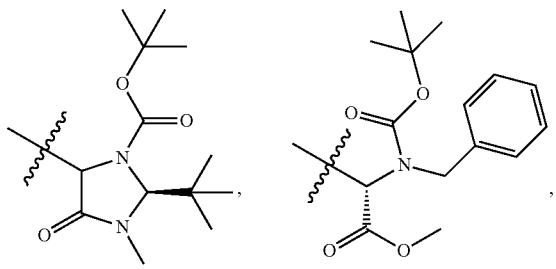

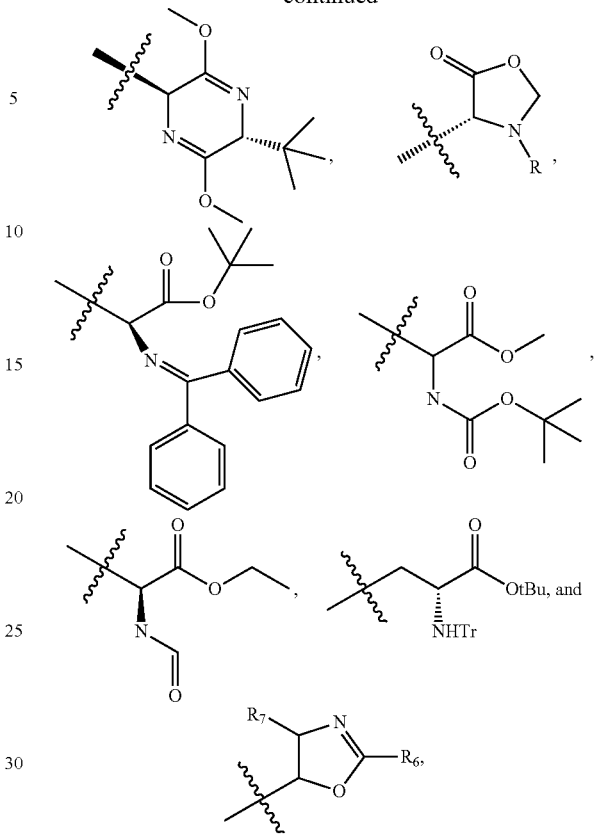

with R being $COCH_3$, $COCF_3$, $CH_2Ph$, BOC, or $COOCH_2Ph$;
with $R_6$ being Me or Ph, and
with $R_7$ being H or $CH_3$;

wherein said stabilizing method comprises a stabilization step of contacting said cold aromatic precursor, said cold aromatic intermediate, and said modified or not 18F radiosynthetic intermediate with one or more compounds being at least one of radical scavengers, reductants, and antioxidants, selected from the group of carbonate ($CO_3^{2-}$), nitrite, thiosulfate, thiosulfite, phosphate, phosphite, hypophosphite, phosphorous acid, a Fe(II) derivative, a Sn(II) derivative, iodide, a phenol derivative, HI, toluene, and dichloromethane.

2. A method for stabilizing, toward decomposition caused by beta and gamma radiations, cold and radiosynthetic intermediates used in a synthesis of 18F radiolabeled aromatic amino acid derivatives, said synthesis comprising at least the steps of:
1) providing a cold aromatic precursor;
2) fluorinating said cold aromatic precursor with 18F so as to obtain a 18F radiosynthetic intermediate, and modifying said 18F radiosynthetic intermediate, or
2) modifying said cold aromatic precursor so as to obtain a cold aromatic intermediate, and fluorinating said cold aromatic intermediate with 18F, so as to obtain in both cases a modified 18F radiosynthetic intermediate, wherein the step of modifying said cold aromatic precursor or 18F radiosynthetic intermediate is at least one of a reduction, an oxidation, a halogenation reaction, and a substitution reaction of one functional group by another functional group;

3) deprotecting and/or hydrolyzing said modified 18F radiosynthetic intermediate so as to obtain said 18F radiolabeled aromatic amino acid derivative, said cold aromatic precursor, said cold aromatic intermediate, and said modified or not 18F radiosynthetic intermediate having the general structure:

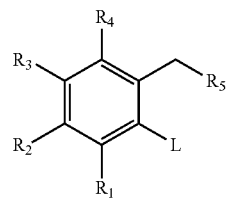

wherein $R_1$, $R_2$, $R_3$, and $R_4$ are selected from the group consisting of H, OH, OMe, OBn, and Oallyl;

wherein L is selected from the group consisting of $NO_2$, $NMe_3^+$, F, $IO_2$,

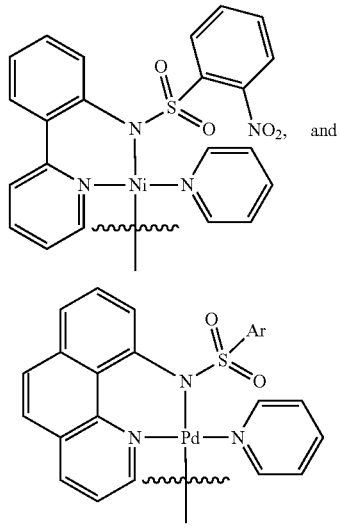

in the case of a cold aromatic precursor or a cold aromatic intermediate and wherein L is $^{18}F$ in the case of a modified or not 18F radiosynthetic intermediate;

wherein $R_5$ is selected from the group consisting of OH, I, Br, Cl,

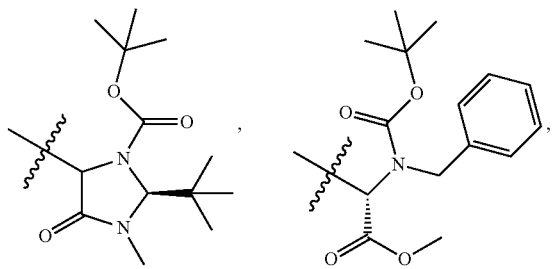

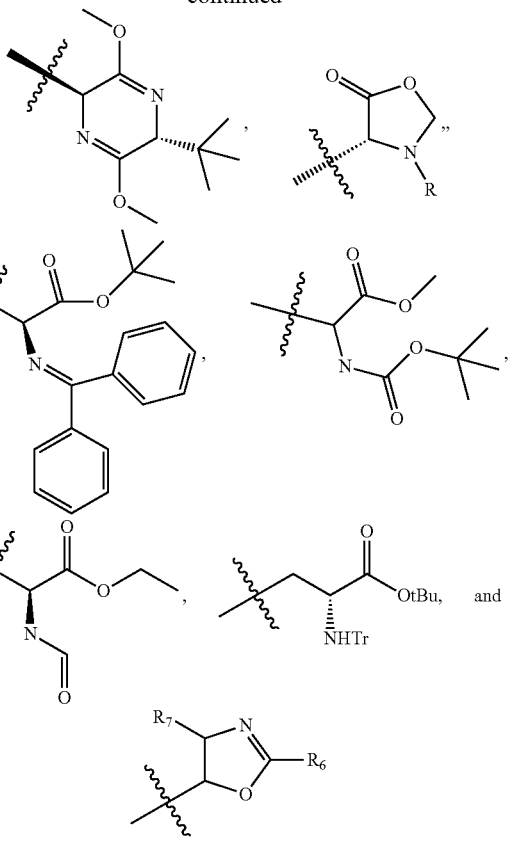

with R being $COCH_3$, $COCF_3$, $CH_2Ph$, BOC, or $COOCH_2Ph$;

with $R_6$ being Me or Ph, and with $R_7$ being H or $CH_3$;

wherein said stabilizing method comprises a stabilization step of contacting said cold aromatic precursor, said cold aromatic intermediate and said modified or not 18F radiosynthetic intermediate with one or more compounds selected from the group consisting of radical scavengers, reductants, and antioxidants;

wherein phosphorous acid is used in the stabilization step of said cold aromatic precursor, said cold aromatic intermediate, and said modified or not 18F radiosynthetic intermediate.

3. A method for stabilizing, toward decomposition caused by beta and gamma radiations, cold and radiosynthetic intermediates used in a synthesis of 18F radiolabeled aromatic amino acid derivatives, said synthesis comprising at least the steps of:

1) providing a cold aromatic precursor;
2) fluorinating said cold aromatic precursor with 18F so as to obtain a 18F radiosynthetic intermediate, and modifying said 18F radiosynthetic intermediate, or
2) modifying said cold aromatic precursor so as to obtain a cold aromatic intermediate, and fluorinating said cold aromatic intermediate with 18F, so as to obtain in both cases a modified 18F radiosynthetic intermediate, wherein the step of modifying said cold aromatic precursor or 18F radiosynthetic intermediate is at least one of a reduction, an oxidation, a halogenation reaction, and a substitution reaction of one functional group by another functional group;

3) deprotecting and/or hydrolyzing said modified 18F radiosynthetic intermediate so as to obtain said 18F radiolabeled aromatic amino acid derivative, said cold aromatic precursor, said cold aromatic intermediate, and said modified or not 18F radiosynthetic intermediate having the general structure:

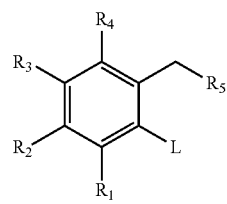

wherein $R_1$, $R_2$, $R_3$, and $R_4$ are selected from the group consisting of H, OH, OMe, OBn, and Oallyl;

wherein L is selected from the group consisting of $NO_2$, $NMe_3^+$, F, $IO_2$,

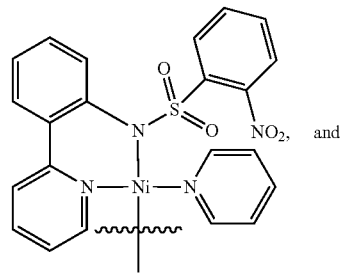

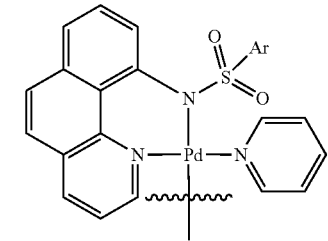

in the case of a cold aromatic precursor or a cold aromatic intermediate and wherein L is $^{18}F$ in the case of a modified or not 18F radiosynthetic intermediate;

wherein $R_5$ is selected from the group consisting of OH, I, Br, Cl,

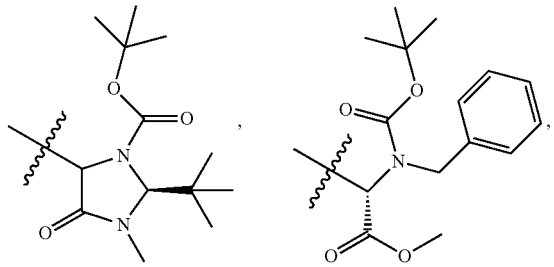

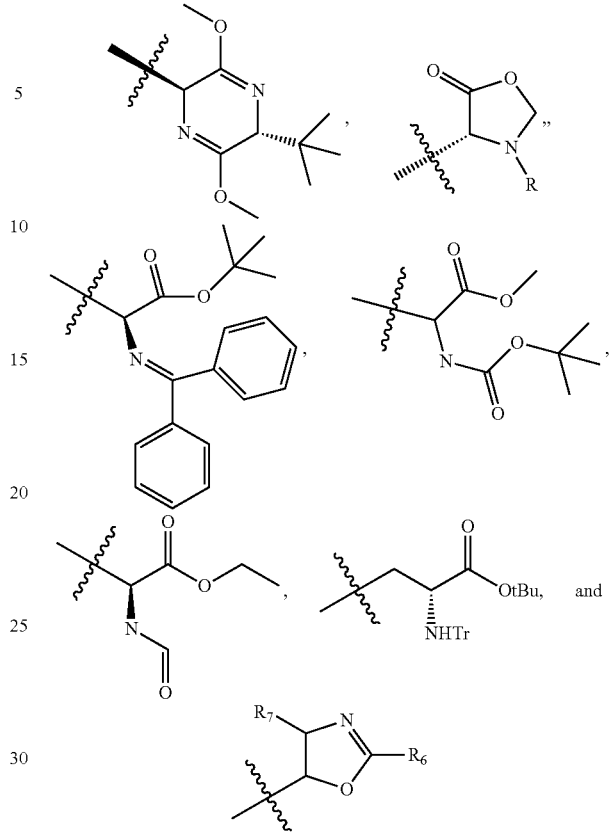

with R being $COCH_3$, $COCF_3$, $CH_2Ph$, BOC, or $COOCH_2Ph$;

with $R_6$ being Me or Ph, and with $R_7$ being H or $CH_3$;

wherein said stabilizing method comprises a stabilization step of contacting said cold aromatic precursor, said cold aromatic intermediate, and said modified or not 18F radiosynthetic intermediate with one or more compounds selected from the group consisting of radical scavengers, reductants, and antioxidants;

wherein a Fe(II) derivative or a Sn(II) derivative is used in the stabilization step of said cold aromatic precursor, said cold aromatic intermediate, and said modified or not 18F radiosynthetic intermediate.

4. The method of claim 1, wherein HI is used in a halogenation step and/or in the deprotection/hydrolysis step.

5. The method of claim 1, wherein the stabilization step occurs after the step of fluorinating said cold aromatic precursor or said cold aromatic intermediate with 18F and/or the step of modifying said 18F radiosynthetic intermediate and/or during the step of deprotecting and/or hydrolyzing said modified 18F radiosynthetic intermediate.

6. The method of claim 1, wherein the compound used in the stabilization step is also involved in the radiosynthetic process as a reagent or as a solvent.

7. The method of claim 1, wherein HI is used both in the stabilization step of the cold and radiosynthetic intermediates as a reagent.

* * * * *